(12) United States Patent
Suehiro et al.

(10) Patent No.: US 7,410,790 B2
(45) Date of Patent: Aug. 12, 2008

(54) METHOD FOR PRODUCING γ-GLUTAMYLCYSTEINE

(75) Inventors: Mariko Suehiro, Kawasaki (JP); Hiroaki Nishiuchi, Kawasaki (JP); Yasushi Nishimura, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 247 days.

(21) Appl. No.: 10/732,523

(22) Filed: Dec. 11, 2003

(65) Prior Publication Data

US 2004/0259230 A1   Dec. 23, 2004

(30) Foreign Application Priority Data

Dec. 13, 2002   (JP)   ............... 2002-361918

(51) Int. Cl.
*C12N 1/14* (2006.01)
*C12N 1/15* (2006.01)
*C12N 1/16* (2006.01)
*C12N 1/18* (2006.01)
*C12N 1/19* (2006.01)
*C12N 15/31* (2006.01)
*C12N 15/52* (2006.01)

(52) U.S. Cl. ............... 435/254.21; 435/243; 435/254.1; 435/254.11; 435/254.2; 435/130; 435/69.1; 426/62

(58) Field of Classification Search ........................ None
See application file for complete search history.

(56) References Cited

U.S. PATENT DOCUMENTS 5,206,220 A * 4/1993 Hilton ........................ 514/19
2003/0124684 A1 7/2003 Nishiuchi et al.

FOREIGN PATENT DOCUMENTS

EP    1 201 747       5/2002
JP    10-33161        2/1998
WO   WO 03/046155     6/2003

OTHER PUBLICATIONS

Shimoi et al., 2000, J. Biosci. Bioengineering, 90, 6:643-647.*
Wang et al., 1997, Biochem J., 322:241-244.*
Polekhina et al., 1999, Embo J., 18:3204-3213.*
Ohtake et al., 1990, Agric. Boil. Chem., 54(12): 3145-3150.*
Rouillon et al., 2000, Embo J., 19(2): 282-294.*
Mestres et al., 2000, J. Chromotography A, 881:569-581.*
Y. Ohtake, et al., Agric. Biol. Chem., vol. 54, No. 12, pp. 3145-3150, "Isolation and Characterization of Glutathione Biosynthesis-Deficient Mutants in Saccharomyces Cerevisiae", May 9, 1990.
Y. Inoue, et al., Biochimica et Biophysica Acta, 1395, pp. 315-320, "Molecular Identification of Glutathione Synthetase (GSH2) Gene From Saccharomyces Cerevisiae", 1998.
D. Thomas, et al., Molecular and Cellular Biology, vol. 15, No. 12, pp. 6526-6534, "MET30P, A Yeast Transcriptional Inhibitor That Responds to S-Adenosylmethionone, is an Essential Protein with WD40 Repeats", Dec. 1995.
H. Shimoi, et al., "Molecular Cloning and Application of a Gene Complementing Pantothenic Acid Auxotrophy of Sake Yeast Kyokai No. 7", *Journal of Bioscience and Bioengineering*, vol. 90, No. 6, pp. 643-647 (2000).

* cited by examiner

*Primary Examiner*—David Guzo
(74) *Attorney, Agent, or Firm*—Oblon, Spivak, McClelland, Maier & Neustadt, P.C.

(57) ABSTRACT

The yeast which has γ-glutamylcysteine-producing ability and is auxotrophic for pantothenic acid is proliferated in a medium containing a sufficient amount of pantothenic acid, and then it is cultured in a medium containing a limited amount of pantothenic acid to increase the γ-glutamylcysteine content in its cells, whereby the yeast in which γ-glutamylcysteine is accumulated is obtained.

8 Claims, 2 Drawing Sheets

METHOD FOR PRODUCING γ-GLUTAMYLCYSTEINE

BACKGROUND OF THE INVENTION

1. Field of the Invention

The present invention relates to a γ-glutamylcysteine-producing yeast strain, to a method for culturing it, and to a food utilizing cells of that yeast strain. A material containing γ-glutamylcysteine and a material containing cysteine produced from γ-glutamylcysteine are useful in the field of foods.

2. Description of the Related Art

Cysteine is used for the purpose of enhancing the flavor of foods or the like. Known production methods of cysteine include, for example, proteolysis method and semi-synthetic method, and these methods are currently used in the main. Although natural food materials having high cysteine contents have been demanded for the purpose of using them to enhance the flavor of foods, such natural food materials have been rarely known. On the other hand, it has been reported that heat- or enzyme-treatment of yeast extracts containing γ-glutamylcysteine may give rise to food materials having high cysteine contents (WO 00/30474).

γ-glutamylcysteine is synthesized from cysteine and glutamic acid as substrates by the function of γ-glutamylcysteine synthetase. On the other hand, glutathione is synthesized from γ-glutamylcysteine and glycine as substrates by the function of glutathione synthetase. It has been reported that a yeast in which glutathione synthetase gene has been disrupted accumulates γ-glutamylcysteine (Otake et al., Agric. Biol. Chem., 54(12), 3145-3150, 1990).

Yeasts having high γ-glutamylcysteine contents have been reported in WO 00/30474, Otake et al., Agric. Biol. Chem., 54(12), 3145-3150, 1990, Chris et al., Molecular Biology of the Cell., 8, 1699-1707, 1997, Inoue et al., Biochimica et Biophysica Acta, 1395, 315-320, 1998, or the like. However, these reports has not disclosed the conditions for culturing the yeast, in which glutathione synthetase gene has been disrupted or weakened, to accumulate a large amount of γ-glutamylcysteine.

A method for culturing a yeast to accumulate a large amount of glutathione, a metabolic product of γ-glutamylcysteine, in its cells has been disclosed (JP 48-92579A and the like). This report describes that an amount of the accumulated glutathione has been increased when cysteine, a glutathione-constituting amino acid, was added during culturing a yeast. Therefore, it is considered that a large amount of γ-glutamylcysteine could be accumulated when cysteine is added during culturing the yeast in which glutathione synthetase gene is disrupted or weakened. However, it is not practical from an economical aspect to add cysteine during culturing a γ-glutamylcysteine-containing yeast for obtaining cysteine-containing materials, since γ-glutamylcysteine-containing materials are useful for producing cysteine-containing materials.

Further, Otake et al. has reported the γ-glutamylcysteine contents in the cells of the yeast YL1 strain, in which a glutathione synthetase gene has been disrupted, when 3 mM of cysteine was added during culturing the yeast (Otake et al., Agric. Biol. Chem., 54(12), 3145-3150, 1990). This report describes that the amount of the accumulated γ-glutamylcysteine was 0.533% when the YL1 strain was cultured in the presence of cysteine, while the amount was 0.518% when the strain was cultured in the absence of cysteine. This result implies that it is not practical to add cysteine during culturing the yeast in which glutathione synthetase gene has been disrupted or weakened.

It has also been reported that glutathione contents in yeast cells has increased when expression of a MET25 gene was enhanced. Further, as a method for increasing expression of the MET25 gene, a method by utilizing a mutant MET4 gene (Omura et al., FEBS Letters 387(1996) 179-183 and JP 10-33161A) and a method by utilizing a mutant MET30 gene (DOMINIQUE et al., MOLECULAR AND CELLUAR BIOLOGY, December 1995, p6526-6534) have been reported.

The mechanism of the expression of the MET25 gene is considered as follows. That is, the MET4 gene product functions as a positive regulator for the expression of the MET25 gene. In general, the MET4 gene product forms a SCFMET30 complex together with the MET30 gene product and other several proteins, and the MET4 gene product is ubiquitinated and decomposed together with the MET30 gene product by a proteolytic system of 26S proteasome, thereby, the expression of the MET25 gene is suppressed. On the other hand, when the function of the SCFMET30 complex is deteriorated, the MET4 gene product and the MET30 gene product are not decomposed and the MET25 gene is expressed (Patton et al., Genes Dev. 12: 692-705, 1998 and Rouillon et al., EMBO Journal 19: 282-294, 2000).

Based on these reports, it is suggested that γ-glutamylcysteine content could also be increased in a yeast having a high γ-glutamylcysteine content by enhancing the expression of the MET25 gene.

In addition, it has been reported that when "sake" yeast was cultured in a calcium panthotenate-deficient condition, the yeast has accumulated hydrogen sulfide in its logarithmic growth phase. This report pays its attention to the generation of hydrogen sulfide from cysteine, and it also describes that the phenomenon is further promoted in a pantothenic acid-deficient condition.

SUMMARY OF THE INVENTION

Under the above-mentioned technical background, an object of the present invention is to provide a yeast strain suitable for the production of γ-glutamylcysteine, a method for producing γ-glutamylcysteine using such a yeast strain, and a γ-glutamylcysteine-containing food or beverage obtainable using such a yeast strain.

The inventors of the present invention have considered that the amount of γ-glutamylcysteine accumulated in yeast cells does not need to be constant during culturing the yeast and that a required amount of γ-glutamylcysteine may be accumulated right before harvesting the yeast cells. Based on the consideration, the inventors of the present invention have made extensive studies and as a result, they have found that the amount of the accumulated γ-glutamylcysteine is increased by culturing a yeast, which has γ-glutamylcysteine-producing ability, and is auxotrophic for pantothenic acid, in a pantothenic acid-limited condition after proliferating the yeast by culturing it in the presence of a minimum amount of pantothenic acid required by the yeast. Thereby, the inventors have achieved the present invention.

That is, the present invention is as follows:

(1) A yeast which has a γ-glutamylcysteine-producing ability and is auxotrophic for pantothenic acid, wherein γ-glutamylcysteine content per dried cells of the yeast increases in course of time when the yeast is cultured in a medium containing a limited amount of pantothenic acid.

(2) The yeast according to (1), which is modified so that intracellular glutathione synthetase activity is reduced or eliminated.

(3) The yeast according to (1) or (2), which is modified so that expression of a MET25 gene is derepressed.

(4) The yeast according to (3), wherein the expression of the MET25 gene is derepressed by harboring the mutant MET30 gene having a mutation which replaces serine at position 569 of a protein encoded by the MET30 gene with an amino acid other than serine.

(5) The yeast according to (4), wherein the amino acid other than serine is phenylalanine.

(6) The yeast according to any one of (1) to (5), which belongs to the genus *Saccharomyces*.

(7) A method for producing a yeast in which γ-glutamylcysteine is accumulated, comprising the step to proliferate the yeast according to any one of (1) to (6) by culturing it in a medium containing a sufficient amount of pantothenic acid, and the step to increase γ-glutamylcysteine content in the yeast cells by culturing it in a medium containing a limited amount of pantothenic acid.

(8) A food or beverage comprising a culture obtained by culturing the yeast according to anyone of (1) to (6) under a suitable condition, a fractionated product of the culture containing γ-glutamylcysteine, or a culture or fractionated product thereof in which cysteine has been produced by a heat treatment.

(9) The food or beverage according to (8), which is selected from the group consisting of an alcoholic beverage, a bread food, and a fermented food flavoring material.

(10) A yeast extract, produced by using a culture obtained by culturing the yeast according to any one of (1) to (6) under a suitable condition.

(11) A method for producing a food or beverage containing γ-glutamylcysteine or cysteine, comprising culturing the yeast according to any one of (1) to (6) under a suitable condition, mixing the obtained culture or fractionated product thereof, or the culture or fractionated product thereof subjected to a heat-treatment with a food or beverage raw material, and processing the mixture into the food or beverage.

(12) A yeast in which expression of a MET25 gene is derepressed by harboring a mutant MET30 gene having a mutation which replaces serine at position 569 of a protein encoded by the MET30 gene with phenylalanine.

DETAILED DESCRIPTION OF THE INVENTION

Hereinafter, the present invention will be described in detail.

<1> Yeast of the Present Invention

The yeast of the present invention has a γ-glutamylcysteine-producing ability and is auxotrophic for pantothenic acid. Further, the yeast of the present invention is a yeast in which γ-glutamylcysteine contents per dried cells of the yeast increases in course of time when it is cultured in a medium containing a limited amount of pantothenic acid.

In the present invention, "a γ-glutamylcysteine-producing ability" means "an ability to accumulate γ-glutamylcysteine in cells in an amount larger than a wild type strain." Preferably, it means an ability to accumulate 1% or more of γ-glutamylcysteine per dried yeast cells when it is cultured in a medium containing a limited amount of pantothenic acid after having been cultured in a medium containing a sufficient amount of pantothenic acid. More preferably, it means that an amount of glutathione accumulated in cells is 0.1% or less per dried yeast cells, in addition to the above-mentioned amount of the accumulated γ-glutamylcysteine.

The accumulated amount of γ-glutamylcysteine or glutathione per dried yeast cells is, for example, the γ-glutamylcysteine or glutathione content (weight %) in yeast cells subjected to heat-treatment of 105° C. for 4 hours.

Examples of the yeast having a γ-glutamylcysteine-producing ability include a yeast whose intracellular glutathione synthetase activity is reduced or eliminated, a yeast modified so that γ-glutamylcysteine synthetase activity is enhanced, or a yeast in which intracellular glutathione synthetase activity is reduced or eliminated and which is modified so that γ-glutamylcysteine synthetase activity is enhanced.

The yeast in which intracellular glutathione synthetase activity is reduced or eliminated can be obtained by gene substitution method using a DNA containing a glutathione synthetase gene (GSH2) which has been modified so as not to produce an enzyme having its normal function by deleting a partial sequence of the gene, or a glutathione synthetase gene having a mutation for reducing its enzymatic activity (to be simply referred to as "mutant GSH2 gene" hereinafter). Moreover, the yeast in which intracellular glutathione synthetase activity is reduced or eliminated can be obtained by subjecting a wild type yeast strain to an ordinary mutation treatment such as UV irradiation or a treatment with a mutagen such as N-methyl-N-nitrosoguanidine (NTG), ethyl methanesulfonate (EMS), nitrous acid, or acridine. It can be confirmed by PCR method or the like that the obtained mutant has a target mutation.

The mutation for reducing glutathione synthetase activity is, for example, a mutation which replaces arginine at position 370 in amino acid sequence of SEQ ID: 2 with a termination codon.

Other examples of mutations for reducing glutathione synthetase activity include the followings (WO 03/046155):

(1) A mutation which replaces threonine at position 47 in amino acid sequence of SEQ ID: 2 with isoleucine.
(2) A mutation which replaces glycine at position 387 in amino acid sequence of SEQ ID: 2 with aspartic acid.
(3) A mutation which replaces proline at position 54 in amino acid sequence of SEQ ID: 2 with leucine.

The above mutations of (1) or (2) can be used alone or in combination but a combination of mutations (1) and (3) and a combination of mutations (2) and (3) are preferred.

Introduction of the above mutations to the glutathione synthetase gene can be carried out by site-directed mutagenesis using synthesized oligonucleotides.

The above-mentioned gene substitution can be carried out as follows. That is, a yeast is transformed with a recombinant DNA containing a mutant GSH2 gene to cause recombination between the mutant GSH2 gene and a chromosomal GSH2 gene. On this occasion, a marker gene inserted in the recombinant DNA depending on the characteristics such as auxotrophy of the host makes the manipulation easy. Furthermore, making the above-mentioned recombinant DNA linear, for example, by cleavage with a restriction enzyme and, in addition, removal of a replication control region that functions in yeasts from the recombinant DNA can efficiently give rise to a strain in which the recombinant DNA is integrated into the chromosome.

For the transformation of yeasts, those methods conventionally used in the transformation of yeasts, such as a protoplast method, a KU method, a KUR method, an electroporation method or the like can be employed. The strain in which the recombinant DNA is integrated into the chromosome in the above-mentioned manner undergoes recombination between the mutant GSH2 gene and the GSH2 gene inherently existing on the chromosome, so that the two fusion genes, i.e., the wild type GSH2 gene and the mutant GSH2 gene, are inserted into the chromosome so that the other parts of the recombinant DNA (vector segment and marker gene) should be present between the two fusion genes.

Next, to leave only the mutant GSH2 gene on the chromosomal DNA, one copy of the GSH2 gene together with the vector segment (including also the marker gene) is removed from the chromosomal DNA by recombination of the two GSH2 genes. On this occasion, there are two cases. In one case, the wild type GSH2 gene is left on the chromosomal DNA and the mutant GSH2 gene is excised therefrom. In another case, on the contrary, the mutant GSH2 gene is left on the chromosomal DNA and the wild GSH2 gene is excised. In both cases, the marker gene is removed so that the occurrence of a second recombination can be confirmed by phenotype corresponding to the marker gene. The objected gene-substituted strain can be selected by amplifying the GSH2 gene by a PCR method and examining its structure.

The mutant GSH2 gene used in gene substitution may be one that encodes full-length glutathione synthetase but may also be a gene fragment that encodes a part of the enzyme as far as it includes the mutation site.

The nucleotide sequence of the glutathione synthetase gene (GSH2) of *Saccharomyces cerevisiae* has been reported (Inoue et al., Biochim. Biophys. Acta, 1395 (1998) 315-320, GenBank Accession No. Y13804, SEQ ID NO: 1) and this gene can be obtained from the *Saccharomyces cerevisiae* chromosomal DNA by PCR method in which oligonucleotides prepared based on the nucleotide sequence is used as primers. The gene used in the gene substitution may also be a gene which is derived from a microorganism other than that belonging to the genus *Saccharomyces*.

The mutant GSH2 gene used in the present invention may be a gene which encodes glutathione synthetase having amino acid sequence of SEQ ID NO: 2 including substitution, deletion, insertion, or addition of one or several amino acids at one or several positions other than the above-mentioned positions of 47, 387 and 54. Although the number of "several" differs depending on the position in the three dimensional structure of the protein or the type of amino acid, it usually means 2 to 10, preferably 2 to 6, more preferably 2 to 3. Alternatively, the mutant GSH2 gene may be a DNA which encodes a protein having homology of not less than 30 to 40%, preferably not less than 55 to 65% with the entire amino acid sequence of SEQ ID NO: 2.

The mutation which causes substitution, deletion, insertion, addition, inversion in a glutathione synthetase sequence also includes a mutation or variation which naturally occurs on the basis of the individual difference or the difference in species or genus of a bacterium which harbors glutathione synthetase gene.

In the case of disrupting a glutathione synthetase gene in a yeast strain, not only full-length glutathione synthetase gene but also fragment of the gene which has a length enough to cause gene disruption can be used. The glutathione synthetase gene used in gene disruption is not particularly limited if it has enough homology to cause homologous recombination with the chromosomal glutathione synthetase gene of the yeast strain. The gene may be obtained from microorganism other than the yeast to be used.

Examples of the DNAs which can cause homologous recombination with the GSH2 gene of *Saccharomyces cerevisiae* include a DNA having homology of 70% or more, preferably 80% or more, more preferably 90% or more to the DNA having nucleotide sequence of SEQ ID NO: 1. Such DNAs include a DNA which is hybridizable with the DNA having nucleotide sequence of SEQ ID NO: 1 under the stringent condition. The stringent condition are exemplified by a condition of washing at a salt concentration corresponding to 60° C., 1×SSC and 0.1% SDS, preferably 0.1×SSC and 0.1% SDS.

The yeast in which glutathione synthetase activity is reduced or eliminated can be obtained by subjecting a wild type yeast to an ordinary mutation treatment such as UV irradiation or a treatment with a mutagen such as N-methyl-N-nitrosoguanidine (NTG), ethyl methanesulfonate (EMS), nitrous acid, or acridine.

A method for raising γ-glutamylcysteine synthetase activity in yeast cells can be exemplified by a method of increasing the copy number of the γ-glutamylcysteine synthetase gene in yeast cells by transforming the yeast with a plasmid containing the gene, or a method of enhancing the transcription of chromosomal γ-glutamylcysteine synthetase gene by replacing its native promoter with a strong promoter (Yasuyuki Otake et al., Bioscience and Industry, Vol. 50, No. 10, pp. 989-994, 1992). γ-glutamylcysteine synthetase gene can be exemplified by that of *Saccharomyces cerevisiae* (GenBank Accession No. D90220).

The intracellular activities of γ-glutamylcysteine synthetase activity and glutathione synthetase activity can be measured by the method of Jackson (Jackson, R. C., Biochem. J., 111, 309 (1969)) and the method of Gushima et al. (Gushima, T. et al., J. Appl. Biochem., 5, 210 (1983)).

The yeast of the present invention has a γ-glutamylcysteine-producing ability and is auxotrophic for pantothenic acid. In the present invention, "auxotrophic for pantothenic acid" means that pantothenic acid is required for the growth of the yeast in a higher concentration than that of pantothenic acid required by a non-modified yeast strain such as a wild type strain.

The mutant which is auxotrophic for pantothenic acid can be obtained by subjecting a yeast to a mutation treatment, replicating the treated yeast both in a medium containing pantothenic acid and in a medium containing no pantothenic acid, and selecting a strain which can not form a colony in a medium containing no pantothenic acid and can form a colony in a medium containing pantothenic acid. The strain which is auxotrophic for pantothenic acid can be concentrated by culturing the yeast subjected to the mutation treatment in a medium which does not contain pantothenic acid but contains an antibiotic such as nystatin which specifically affects proliferating-cells.

The medium which does not contain pantothenic acid can be exemplified by a medium having the following composition.

TABLE 1

| Composition | Concentration |
| --- | --- |
| Glucose | 3 g/dl |
| $KH_2PO_4$ | 0.15 g/dl |

TABLE 1-continued

| Composition | Concentration |
| --- | --- |
| $MgSO_4 \cdot 7H_2O$ | 0.17 g/dl |
| $CaCl_2 \cdot 2H_2O$ | 0.03 g/dl |
| Urea | 0.4 g/dl |
| Biotin | 1.5 ppm |
| Inositol | 100 ppm |
| V.B6 | 0.05 ppm |
| Zn ion | 0.3 ppm |
| Fe ion | 0.3 ppm |
| Cu ion | 0.05 ppm |

The medium containing pantothenic acid can be obtained, for example, by adding 0.1 to 10 mg/L, preferably, 0.4 mg/L of pantothenic acid salt to the above medium. The pantothenic acid salt can be added, for example, as calcium pantothenate. In the case of a solid medium, the medium may contain a suitable amount of agar.

The yeast of the present invention having the above-mentioned properties can be proliferated in a medium containing a sufficient amount of pantothenic acid, and then, the yeast is cultured in a medium containing a limited amount of pantothenic acid, thereby, the γ-glutamylcysteine content per dried cells increases in course of time. "Sufficient amount of pantothenic acid" means the amount under which a yeast in logarithmic growth phase can proliferate. This amount is generally 0.1 mg/L or more, preferably 0.4 mg/L or more. Although the upper limit of the amount is not particularly limited, the amount of 10 mg/L or more is ordinary excessive. Therefore, the amount of pantothenic acid is generally 0.1 to 10 mg/L.

"Limited amount of pantothenic acid" means the limited amount under which a yeast in logarithmic growth phase which had been cultured in a medium containing a sufficient amount of pantothenic acid cannot grow or can grow at a reduced rate. The limited amount is generally 0.1 mg/L or less, preferably 0.01 mg/L or less. The limited amount of pantothenic acid may be 0 mg/L.

"γ-glutamylcysteine content per dried yeast cells increases in course of time" means that, when the yeast of the present invention is cultured in a medium containing the limited amount of pantothenic acid after it had been cultured in a medium containing the sufficient amount of pantothenic acid, the maximum γ-glutamylcysteine content increases preferably not less than 1.5 times, more preferably not less than 1.8 times, particularly preferably not less than 2 times as much as the γ-glutamylcysteine content per dried yeast cells after the time of changing the medium.

The yeast of the present invention may be a yeast which is modified so that expression of the MET25 gene is derepressed. "The expression of the MET25 gene is derepressed" means that the expression of the MET25 gene is not repressed by methionine under the conditions disclosed by the report of DOMINIQUE et al. (MOLECULAR AND CELLUAR BIOLOGY December, 1995, p 6526-6534).

A method for derepressing the expression of the MET25 gene can be exemplified by a method of transforming a yeast with a mutant MET30 gene encoding a protein having amino acid sequence of SEQ ID: 4 in which serine at position 569 is replaced with an amino acid other than serine. "Amino acid other than serine" is, for example, phenylalanine. The yeast having the above-mentioned property can be obtained by subjecting a yeast to a mutation treatment as shown in Examples which is described hereinafter. Since a desired mutation is specified as described above, the yeast having such a mutation can be easily obtained by a genetic engineering technology. For example, the yeast in which expression of the MET25 gene is derepressed can be obtained by gene substitution using the above-mentioned mutant MET30 gene. The gene substitution can be carried out in the same manner as the above-mentioned GSH2 gene. The yeast harboring the mutant MET30 gene can also be obtained by transforming the yeast with a plasmid including the mutant MET30 gene to increasing the copy number of the mutant gene. Further, the yeast harboring a mutant MET30 gene can also be obtained by subjecting a wild type yeast to a ordinary mutation treatment such as UV irradiation, or a treatment with a mutagen such as N-methyl-N-nitrosoguanidine (NTG), ethyl methanesulfonate (EMS), nitrous acid, or acridine as described in Examples. It can be confirmed by PCR, for example, that the obtained mutant strain has a desired mutation. The strain which harbors a mutant MET30 gene encoding the protein having amino acid sequence of SEQ ID: 4 in which serine at position 569 is replaced with phenylalanine can be used for producing glutathione.

The MET30 gene is a gene which can form a SCFMET30 complex with a MET4 gene product and other several proteins, and encodes a protein involved in the regulation of expression of the MET25 gene. As a MET30 gene, there can be exemplified a MET30 gene derived from *Saccharomyces cerevisiae* having nucleotide sequence of SEQ ID NO: 3, or a homologue thereof. The homologue can be exemplified by a DNA which is hybridizable with a DNA having nucleotide sequence of SEQ ID NO: 3 under the stringent condition. The "stringent condition" herein used means a condition where a so-called specific hybrid is formed but not any non-specific hybrid is not formed. While it is difficult to numerically define the condition, exemplary conditions include one allowing hybridization of DNAs having a high homology, for example, a homology of 50% or more, but not allowing hybridization of DNAs having a homology of less than 50%, or conditions under which DNAs are hybridized with each other at a salt concentration corresponding to an ordinary conditions of washing in Southern hybridization, i.e., 60° C., 1×SSC and 0.1% SDS, preferably 0.1×SSC and 0.1% SDS.

"Serine at position 569" means a serine residue located at position 569 in the amino acid sequence of SEQ ID NO: 4. A position of an amino acid residue in an amino acid sequence may be changed by insertion, deletion, or the like in a upstream region of the residue. In the present invention, "the serine at position 569" may be an amino acid residue corresponding to the serine residue at position 569 in the amino acid sequence of SEQ ID NO: 4 in the case that the absolute position in the amino acid sequence has been changed as described above.

The mutant MET30 gene used in the present invention may be a conservative variant which encodes a protein having the same function as the protein having amino acid sequence of SEQ ID NO: 4, that is, a mutant MET30 encoding a protein having an amino acid sequence of SEQ ID NO: 4 including substitution, deletion, insertion, or addition of one or several amino acids at one or more positions other than position 569. Although the number of the "several" amino acids differs depending on the position in the three dimensional structure of the protein or the type of an amino acid, it usually means 2 to 10, preferably 2 to 6, more preferably 2 to 3. Alternatively, the mutant MET30 gene may be a DNA which encodes a protein having homology of not less than 30 to 40%, preferably not less than 55 to 65% with the entire amino acid sequence of SEQ ID NO: 4.

The mutation which causes substitution, deletion, insertion, addition, inversion in amino acid sequence of the MET30 protein also includes mutation or variation which naturally occurs on the basis of the individual difference or the difference in species or genus of a bacterium which harbors the MET30 gene.

The yeast of the present invention is not particularly limited as long as it can produce γ-glutamylcysteine and, for example, includes a yeast belonging to the genus *Saccharomyces* such as *Saccharomyces cerevisiae*, a yeast belonging to the genus *Candida* such as *Candida utilis*, and a yeast belonging to the genus *Schizosaccharomyces* such as *Schizosaccharomyces pombe*. The yeast strain of the present invention may be a haploid, but polyploidy of diploid or more is preferred since polyploidy strain is superior in growth.

The polyploidy strain having a γ-glutamylcysteine-producing ability can be obtained by subjecting a polyploidy strain to a mutation treatment and screening a strain having a γ-glutamylcysteine-producing ability, or mating a haploid strain used in breeding the γ-glutamylcysteine-producing haploid strain with a wild type haloid strain, allowing obtained diploid strain to form spores, selecting a strain which shows a reduced glutathione synthetase activity and has a γ-glutamylcysteine-producing ability, mating two of the obtained γ-glutamylcysteine-producing haploid strains which have different mating types with each other. According to a similar method, a strain of triploid or more having γ-glutamylcysteine-producing ability can be obtained.

The methods of breeding and modifying yeasts as described above are disclosed in the first edition of "Chemistry and Life, Experimental Line 31, Yeast Experimental Technology" published by Hirokawa Shoten, first edition of "Bio Manual Series 10, Gene Experimental Method using Yeast" published by Yohdosha, "METHODS in YEAST GENETICS 2000 Edition" published by Cold Spring Harbor Laboratory Press, or the like.

<2> Utilization of the Yeast of the Present Invention

The yeast in which γ-glutamylcysteine is accumulated can be obtained by proliferating the yeast of the present invention by culturing it in a medium containing a sufficient amount of pantothenic acid, and then increasing the intracellular γ-glutamylcysteine content by culturing it in a medium containing a limited amount of pantothenic acid.

Preferably, the "sufficient amount" of pantothenic acid can be determined by measuring experimentally the amount of pantothenic acid required for obtaining a given amount of yeast cells in advance, and then calculating the amount of pantothenic acid required for obtaining a desired amount of yeast cells.

In the step of culturing a yeast for its proliferation, the pantothenic acid may be added in its entire amount before the initiation of cultivation, or divided into portions and added portionwise during the cultivation. The culture medium and culture condition are not particularly limited as long as they can control the amount of pantothenic acid, and a medium and condition generally used for producing yeast extracts or the like can be employed.

In a preferred embodiment of the present invention, a conventional medium for industrial use can be employed, because the yeast with decreased glutathione synthetase activity can grow well in a medium containing no glutathione. Necessary nutrients may optionally be added to the medium depending on the characteristics of the yeast to be used.

After proliferating the yeast to obtain a sufficient amount of yeast cells, the yeast cells are cultured in a medium containing a limited amount of pantothenic acid. For example, a yeast is cultured in a medium containing a sufficient amount of pantothenic acid and then, the obtained culture or yeast cells is transferred to a medium containing a limited amount of or no pantothenic acid. Alternately, without changing the medium, the amount of pantothenic acid can be limited by terminating the addition of another portion of pantothenic acid. The amount of pantothenic acid is preferably limited when a yeast is in its logarithmic growth phase. In the case of using baker s yeast, for example, a culture obtained by culturing the yeast by its logarithmic growth phase or stationary phase is inoculated at the concentration of 2% in a nutrition medium, and cultured with shaking at 30° C. for 8 to 16 hours, thereby yeast cells in a logarithmic growth phase can be obtained.

During the step of culturing the yeast in a medium containing a limited amount of pantothenic acid, the amount of γ-glutamylcysteine accumulated in the yeast cells increases in course of time. Preferably, cultivation is terminated when the amount of accumulated γ-glutamylcysteine has reached a desired amount. Generally, under a preferred condition, the cultivation time is 10 to 30 hours, preferably, 15 to 27 hours.

The obtained culture or the fractionated product thereof contains γ-glutamylcysteine. The culture may be a culture medium containing the yeast cells, or yeast cells collected from the culture medium, cell homogenates, or cell extracts (yeast extract). A fractionated product containing γ-glutamylcysteine may also be obtained from the cell homogenates or the yeast extract.

Cysteine is dissociated from γ-glutamylcysteine by heating the above-described culture which contains γ-glutamylcysteine or fractionated product thereof.

Preparation of a yeast extract and the like may be performed in the same way as a conventional method for preparing a yeast extract. The yeast extract may be obtained by treating the yeast cells subjected to extraction with hot water, or by treating the yeast cells subjected to digestion.

The above-described culture containing γ-glutamylcysteine or cysteine or the fractionated product thereof can be used for producing foods and beverages. The foods and beverages include alcoholic beverages, bread foods, and fermented food flavoring materials. The generation of cysteine by heat-treatment of γ-glutamylcysteine may be carried out during or after producing foods and beverages.

The above-described foods and beverages are produced by mixing the culture or the fractionated product thereof with raw materials of the foods and beverages, and processing the mixture into foods and beverages. The foods and beverages according to the present invention can be produced by using the same raw materials as those used for usual foods and beverages except that the above-mentioned culture or the fractionated product is used. Such raw materials include, for example, rice, barley, cornstarch, etc. for alcoholic beverages; wheat flour, sugar, table salt, butter, fermentation yeast, etc. for bread foods; and soybean, wheat, etc. for fermented food flavoring materials.

EXAMPLES

Hereinafter, the present invention will be described in more detail with reference to examples.

Example 1

<1> Breeding of a Yeast in which Glutathione Synthetase Activity is Reduced

A commercially available diploid *Saccharomyces cerevisiae* used for foods was allowed to form spores according to a conventional method. A haploid yeast, YN0001 strain (MAT α) was obtained from the spores using the random spore method. The YN0001 strain was subjected to a mutation treatment with EMS, and the mutant YN0002 strain (MAT α) having a decreased glutathione content was screened from the mutants. The tetrad analysis proved that a GSH2 gene of the YN0002 strain was mutated. Specifically, glycine at position 387 of the protein encoded by the GSH2 gene was replaced with aspartic acid. In addition, the mutant YN0003 strain (MAT a) having decreased glutathione content was also obtained.

The mutation treatment was carried out under a condition that the mortality was 90%. The YN0001 strain was cultured with shaking in 50 ml of YPD medium at 30° C. for one day. The yeast cells were collected and washed with 0.2M sodium phosphate buffer (pH 7.5) three times. The yeast cells were suspended in a solution containing 9.2 ml of 0.2M sodium phosphate buffer (pH 7.5), 0.5 ml of 40% D-glucose, and 0.3 ml of EMS (Nacalai Tesque, Inc., Code 155-19), and cultured with shaking at 30° C. for 90 minutes. 10 ml of 10% sodium thiosulfate (filter sterilized) was added to the suspension and left to stand at room temperature for 10 minutes to neutralize the mutagen. The yeast cells were collected and washed with 0.2M sodium phosphate buffer (pH 7.5).

The YN0001 strain and the YN0002 strain were respectively inoculated in YPD medium and cultured with shaking at 30° C. The obtained culture were inoculated in SD medium at the concentration of 2% and cultured with shaking at 30° C. The glutathione content in the yeast cells in the logarithmic growth phase was measured. As a result, the glutathione content of the YN0001 strain was 0.52%. On the other hand, the glutathione content of the YN0002 strain was 0.006% or less.

<2> Breeding of a Mutant Strain in which MET30 Gene is Mutated

The aforementioned haploid YN0001 strain (MATα) was subjected to a mutation treatment with EMS in the same manner as described above, and the mutant AJ14819 strain (MATα) in which expression of MET25 gene is not suppressed by methionine was obtained from the mutants. The strain was designated as a private number AJ14819, and was deposited, on Sep. 11, 2002, at National Institute of Advanced Industrial Science and Technology, International Patent Organism Depositary (Central-6, 1-1, Higashi 1-Chome, Tsukuba-shi, Ibaraki-ken, 305-8566, Japan), under the accession number of FERM P-19007. Then, the deposit was converted to an international deposit under the provisions of the Budapest Treaty on Oct. 1, 2003, and received an accession number of FERM BP-08502.

Whether expression of the MET25 gene is suppressed by methionine or not may be determined by examining the ability of a strain to grow on a medium containing selenium (DOMINIQUE et al., MOLECULAR AND CELLUAR BIOLOGY, December 1995, p. 6526-6534). Specifically, screening of a mutant was performed as follows. That is, a yeast that had been subjected to a mutation treatment was spread on YPD agar medium so that about 100 yeast cells could appear on the agar medium. The yeast strains appeared on the YPD medium were inoculated in a medium containing selenium as well as in a medium containing no selenium (the aforementioned agar medium described by DOMINIQUE et al.), by a replica method. A yeast strain which can not grow in the medium containing selenium but can grow in the medium containing no selenium was selected.

Whether the expression of the MET25 gene was increased in the selected strains was determined according to the following procedure. The selected yeast strains and the YN0001 strain were cultured in SD medium, respectively, and the yeast cells were collected at their logarithmic growth phases. Then, RNA in the cells was isolated, and the amount of the transcribed products of the MET25 gene in the isolated RNA was quantified using ACT1 gene as an internal standard. The quantification was carried out by using the apparatus for quantitative PCR (PCR 5700, Applied Biosystems) and TAQ-MAN One-Step RT-PCR kit (Applied Biosystems). ACT1-986T (SEQ ID NO: 5) and MET25-1077T (SEQ ID NO: 6) were used as TAQMAN Probe (Applied Biosystems). ACT1-963F primer (SEQ ID NO: 7) and ACT1-1039R primer (SEQ ID NO: 8) were used for amplification of the ACT1 gene, and MET251056F primer (SEQ ID NO: 9) and MET25-1134R primer (SEQ ID NO: 10) were used for amplification of the MET25 gene (Applied Biosystems). As a result, there was obtained the yeast AJ14819strain in which expression of the MET25 gene increased twice or more compared with that of the YN0001 strain.

The mutated gene in the obtained AJ14819 strain was specified by a tetrad analysis, and the sequence of the gene was determined. As a result, it was found that serine at position 569 of a protein encoded by the MET30 gene was replaced with phenylalanine. According to the above-described procedure, the yeast AJ14819 strain in which expression of the MET25 gene is not suppressed by methionine was obtained.

<3> Breeding of a Yeast which is Auxotrophic for Calcium Pantothenate

The aforementioned haploid yeast YN0001 strain (MATα) was subjected to a mutation treatment with EMS in the same manner as described above. In order to obtain a yeast which is auxotrophic for calcium pantothenate from the mutant strains, the strains were cultured at 30° C. for 2 hours in a medium which contains no calcium pantothenate and to which nystasin (10 μg/ml) was added, and then the cultured medium was spread on YPD agar medium. The appeared mutant strains were inoculated on an agar medium containing no calcium pantothenate and an agar medium containing calcium pantothenate (each of the agar media has the composition shown in Table 1) by a replica method. Then, a yeast that cannot grow in the former agar medium but can grow in the latter agar medium was selected. According to these procedures, the yeast Pa0001 strain (MATa) which is auxotrophic for calcium pantothenate was obtained.

<4> Breeding of a Yeast (GMP Strain; Diploid gsh2 met30 pa-) which is Auxotrophic for Calcium Pantothenate and in which Both a GSH2 Gene and a MET30 Gene are Mutated According to a conventional method, the AJ14819 strain and Pa0001 strain were mated together to obtain a diploid. The resultant diploid was allowed to form spores, and the haploid yeast MP strain (MATa) which harbors a mutant MET30 gene and is auxotrophic for calcium pantothenate was obtained by a random spore analysis. Subsequently, the MP strain and the YN0002 strain were mated together to obtain a diploid strain. The resultant diploid was allowed to form spores, and the haploid yeast GMP-1 strain (MATα) and GMP-2 strain (MATa) each harboring mutant GSH2 gene and mutant MET30 gene and showing calcium pantothenate auxotrophy were obtained by the random spore analysis. The GMP-1 strain and the GMP-2 strain were mated together and thereby the diploid yeast GMP strain was obtained.

<5> Production of γ-glutamylcysteine Using the GMP Strain

Figure 1:
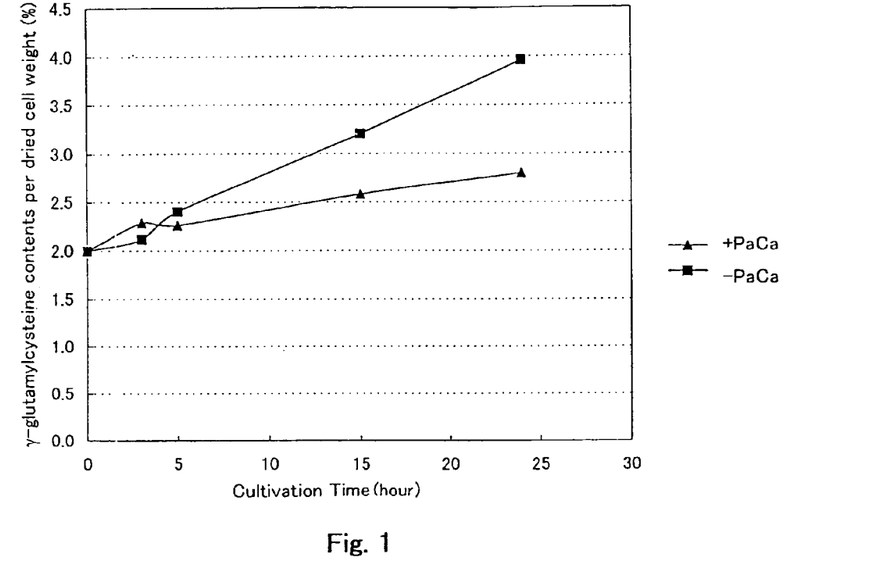
FIG. 1 is a graph showing time course of γ-glutamylcysteine contents in cells of the yeast GMP strain which was cultured in a medium containing or not containing calcium pantothenate (PaCa).

The GMP strain was inoculated in YPD medium (4 ml in test tube), and cultured with shaking at 30° C. for one day. The obtained culture was inoculated in a medium containing 0.4 mg/dl of calcium pantothenate, and cultured with shaking at 30° C. At its logarithmic growth phase, an aliquot of the medium containing yeast cells was picked up and the aliquot was added to a medium containing no calcium pantothenate or a medium containing 0.4 mg/L of calcium pantothenate (Table 1), respectively, at a concentration of 60 mg (dried yeast weight)/dl (medium) and each strain was cultured. The γ-glutamylcysteine content per dried yeast cells was measured in time course. The results are shown in FIG. 1. When the strain was cultured in a medium containing no calcium pantothenate, the γ-glutamylcysteine content increased in course of time at higher rate than in the case where it was cultured in a medium containing a high concentration of calcium pantothenate.

The above-described results revealed that the γ-glutamylcysteine content in the GMP strain increases according to the lack of calcium pantothenate.

Comparative Example 1

Breeding of a Yeast Harboring the Mutant GSH2 Gene and Mutant MET30 Gene

According to the conventional method, the aforementioned AJ14819 strain harboring the mutant MET30 gene and the haploid Pa0001 strain obtained from a commercially available yeast were mated together to obtain a diploid. The obtained diploid was allowed to form spores, and the haploid yeast M strain (MATa) harboring the mutant MET30 gene was obtained by a random spore analysis. Subsequently, the M strain and the aforementioned YN0002 strain harboring the mutant GSH2 gene were mated together to obtain a diploid. The obtained diploid was allowed to form spores, the haploid GM-1 strain (MATα) and GM-2 strain (MATa) each harboring the mutant GSH2 gene or the mutant MET30 gene were obtained by random spore analysis. The GM-1 strain and the GM-2 strain were mated together to obtain the diploid yeast GM strain.

Example 2

Production of γ-glutamylcysteine Using GMP Strain and GM Strain

Figure 2:
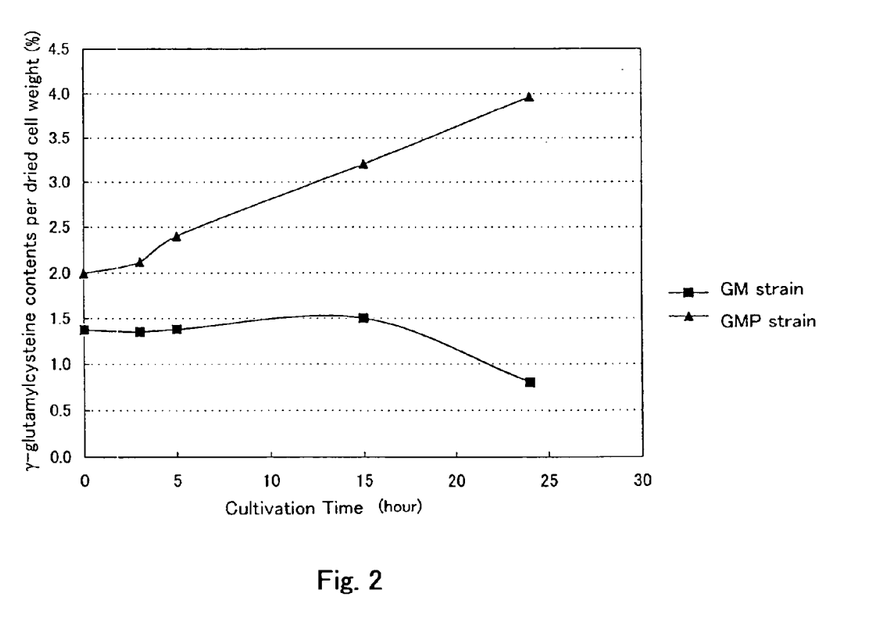
FIG. 2 is a graph showing the comparison of γ-glutamylcysteine contents between GM strain and GMP strain.

The GM strain and the GMP strain were respectively inoculated in YPD medium and cultured with shaking at 30° C. The obtained culture was inoculated in a medium containing 0.4 mg/dl of calcium pantothenate and cultured with shaking at 30° C. At their logarithmic growth phases, the cells were collected and inoculated in a medium containing no calcium pantothenate at the concentration of 60 mg (dried yeast weight)/dl (medium) and cultured with shaking at 30° C. The γ-glutamylcysteine content per dried yeast cells was measured in time course. The results are shown in FIG. 2.

The results show that the γ-glutamylcysteine content per dried yeast cells of GMP strain increases in course of time when it is cultured under the condition lacking calcium pantothenate.

Example 3

Breeding of a Yeast (AJ14861 Strain) which is Auxotrophic for Calcium Pantothenate, in which MET30 Gene is Mutated and GSH2 Gene is Disrupted <1> Preparation of a Cassette for Disruption of a Glutathione Synthetase Gene PCR was performed using GSH2-AUR1-C-F (SEQ ID NO: 11) and GSH2-AUR1-C-R (SEQ ID NO: 12) as primers and pAUR123 vector (Takara Shuzo code No. 3602) digested with KpnI as a template under the following condition:

| | |
|---|---|
| pAUR123 vector digested with KpnI | 1 μl |
| 10 X PCR buffer (MgCl₂ free) | 5 μl |
| dNTP | 4 μl |
| 10 pmol/μl GSH2-AUR1-C-F primer | 1 μl |
| 10 pmol/μl GSH2-AUR1-C-R primer | 1 μl |
| KOD Dash DNA polymerase (Takara Shuzo code LDP-101) | 0.5 μl |
| Purified water | 37.5 μl |
| Total | 50 μl |

The PCR reaction was performed by repeating a cycle consisting of reactions at 94° C. for 40 second, 54° C. for 40 second, 74° C. for 1 minute for 30 cycles.

The obtained PCR product contains sequences of N-terminal region and C-terminal region of the open reading frame of GSH2 gene which are intervened by AUR1-C gene, thereby it can be used to disrupt GSH2 gene.

<2> Breeding of a Yeast in which Glutathione Synthetase Gene is Disrupted

Using the cassette prepared as described above, disruption of the GSH2 gene in the GMP strain was performed as follows. That is, the GMP strain was cultured in YPD medium and the cells were collected at the logarithmic growth phase. The collected cells were washed twice with 1M sorbitol solution and suspended in a solution having the composition of 0.1M LiCl, 10 mM DTT, 10 mM Tris-HCl (pH 7.5), 1 mM EDTA and left to stand at 5° C. for 1 hour. Then, the cells were washed twice with 1M sorbitol solution. The prepared cells were mixed with the above-described PCR product and electroporation was performed using this mixture according to the method described in "Bio Manual Series 10, Experimental Techniques on Yeasts", First edition, Youdosha. The cells subjected to electroporation were inoculated in YPD medium and cultured at 30° C. for 16 hours. Then, the obtained culture was spread onto YPD agar plate containing 0.2 μg/ml of aureobandin A (Takara Shuzo code 9000) as a selection marker and cultured at 30° C. for 3 days. Note that the minimum concentration of aureobandin A to inhibit the growth of GMP strain is 0.05 μg/ml. The appeared colonies were plated onto YPD agar plate containing 0.2 μg/ml of aureobandin A again and colonies resistant to aureobandin A were selected. The strain was designated as a private number of AJ14861, and was deposited, on Nov. 19, 2003, at National Institute of Advanced Industrial Science and Technology, International Patent Organism Depositary (Central-6, 1-1, Higashi 1-Chome, Tsukuba-shi, Ibaraki-ken, 305-8566, Japan) as an international deposit under the provisions of the Budapest Treaty and received an accession number of FERM BP-08553.

<3> Production of γ-glutamylcysteine Using the AJ14861 Strain

Figure 3:
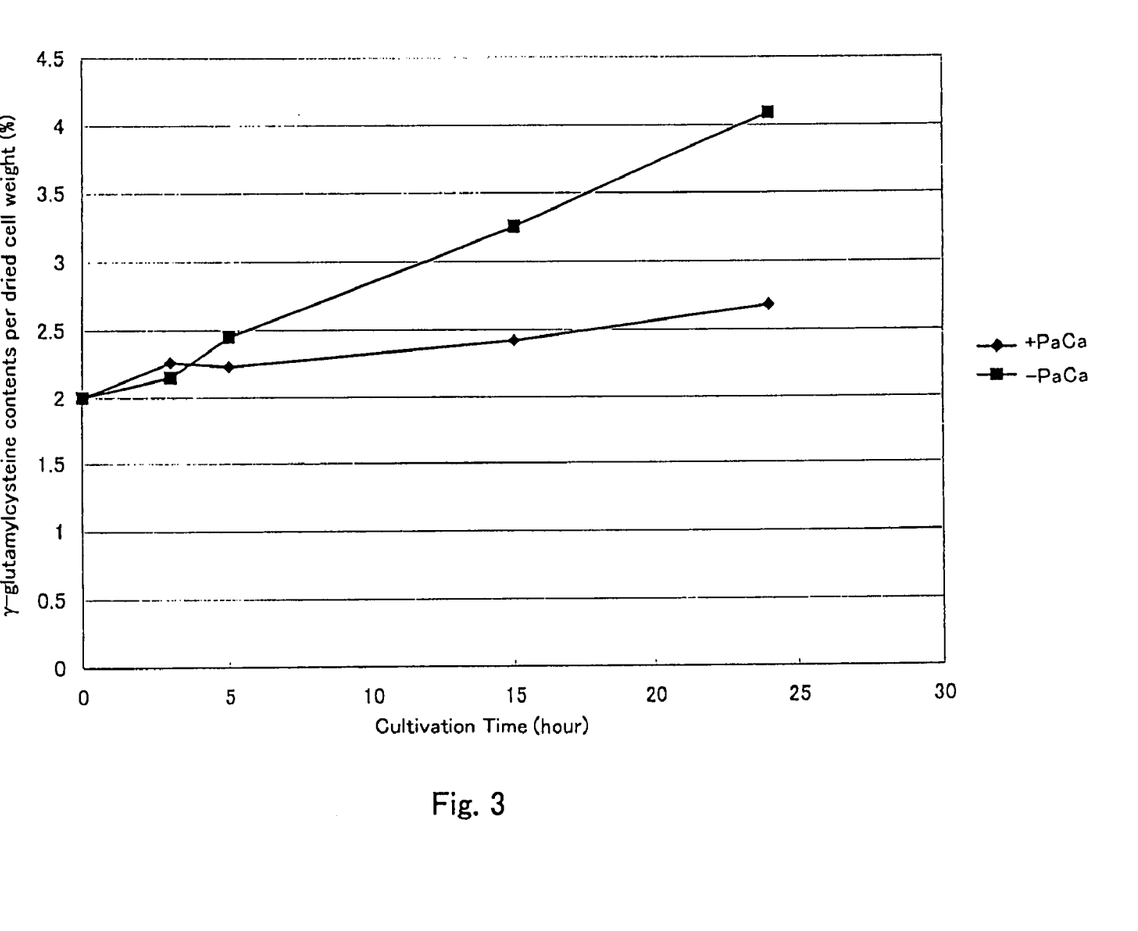
FIG. 3 is a graph showing time course of γ-glutamylcysteine contents in cells of the yeast AJ14861 strain which was cultured in a medium containing or not containing calcium pantothenate.

The AJ14861 strain was inoculated in YPD medium (4 ml in test tube), and cultured with shaking at 30° C. for one day. The obtained culture was inoculated in a medium containing 0.4 mg/dl of calcium pantothenate, and cultured with shaking at 30° C. At its logarithmic growth phase, an aliquot of the medium containing yeast cells was picked up and the aliquot was added to a medium containing no calcium pantothenate or a medium containing 0.4 mg/L of calcium pantothenate (Table 1), respectively, at an concentration of 60 mg (dried yeast cells)/dl (medium) and each strain was cultured. The γ-glutamylcysteine contents per dried yeast cells was measured in time course. The results are shown in FIG. 3. When the strain was cultured in a medium containing no calcium pantothenate, the γ-glutamylcysteine content increased in course of time at higher rate than in the case where it was cultured in a medium containing a high concentration of calcium pantothenate.

The above-described results revealed that the γ-glutamylcysteine content in the AJ14861 strain increases according to the lack of calcium pantothenate.

INDUSTRIAL APPLICABILITY

The present invention provides a yeast which is auxotrophic for pantothenic acid, in which glutathione synthetase activity is reduced or eliminated and the expression of the MET25 gene is derepressed. By culturing the yeast of the present invention under preferable condition, a yeast-culture medium containing a high concentration of γ-glutamylcysteine can be obtained. The yeast and yeast-cultured medium of the present invention can be used in the production of foods and beverages containing γ-glutamylcysteine or cysteine.

What is claimed is:

1. An isolated yeast which has a γ-glutamylcysteine-producing ability and is auxotrophic for pantothenic acid, wherein γ-glutamylcysteine content per dried cells of the yeast increases in course of time when the yeast is cultured in a medium containing a limited amount of pantothenic acid, wherein said yeast comprises a mutated endogenous chromosomal polynucleotide sequence encoding glutathione synthetase wherein said mutation reduces or eliminates glutathione synthetase activity, and wherein said yeast further comprises a mutated MET30 gene wherein the mutation replaces serine at position 569 of a protein encoded by the MET30 gene with phenylalanine and wherein expression of said mutated MET30 gene derepresses expression of the endogenous MET25 gene, wherein said polynucleotide encoding said glutathione synthetase hybridizes with the polynucleotide of SEQ ID NO: 1 under stringent conditions, wherein said MET30 gene hybridizes with the polynucleotide of SEQ ID NO: 3 under stringent conditions, and wherein said stringent conditions comprise washing at 60° in 0.1×SSC and 0.1% SDS.

2. The yeast according to claim 1, which belongs to the genus *Saccharomyces*.

3. A method for producing a yeast in which γ-glutamylcysteine is accumulated, comprising the step to proliferate the yeast according to claim 1 by culturing it in a medium containing a sufficient amount of pantothenic acid, and the step to increase γ-glutamylcysteine content in the yeast cells by culturing it in a medium containing a limited amount of pantothenic acid.

4. A food or beverage comprising a culture obtained by culturing the yeast according to claim 1 under a suitable condition.

5. A method for producing a food or beverage containing γ-glutamylcysteine or cysteine, comprising culturing the yeast according to claim 1 under a suitable condition, mixing the obtained culture or fractionated product thereof, or the culture or fractionated product thereof subjected to a heat-treatment with a food or beverage raw material, and processing the mixture into the food or beverage.

6. The food or beverage according to claim 4, which is selected from the group consisting of an alcoholic beverage, a bread food, and a fermented food flavoring material.

7. The food or beverage according to claim 4, wherein said culture is heat treated to produce cysteine.

8. A yeast in which expression of a MET25 gene is derepressed by harboring a mutant MET30 gene having a mutation which replaces serine at position 569 of a protein encoded by the MET30 gene with phenylalanine, wherein said MET30 gene hybridizes with the polynucleotide of SEQ ID NO: 3 under stringent conditions, and wherein said stringent conditions comprise washing at 60° C. in 0.1×SSC and 0.1% SDS.

* * * * *

SEQUENCE LISTING

<160> NUMBER OF SEQ ID NOS: 12

<210> SEQ ID NO 1
<211> LENGTH: 2466
<212> TYPE: DNA
<213> ORGANISM: Saccharomyces cerevisiae
<220> FEATURE:
<221> NAME/KEY: CDS
<222> LOCATION: (1)..(1476)

<400> SEQUENCE: 1

```
atg gca cac tat cca cct tcc aag gat caa ttg aat gaa ttg atc cag      48
Met Ala His Tyr Pro Pro Ser Lys Asp Gln Leu Asn Glu Leu Ile Gln
1               5                   10                  15 gaa gtt aac caa tgg gct atc act aat gga tta tcc atg tat cct cct      96
Glu Val Asn Gln Trp Ala Ile Thr Asn Gly Leu Ser Met Tyr Pro Pro
            20                  25                  30 aaa ttc gag gag aac cca tca aat gca tcg gtg tca cca gta act atc    144
Lys Phe Glu Glu Asn Pro Ser Asn Ala Ser Val Ser Pro Val Thr Ile
        35                  40                  45 tat cca acc cca att cct agg aaa tgt ttt gat gag gcc gtt caa ata    192
Tyr Pro Thr Pro Ile Pro Arg Lys Cys Phe Asp Glu Ala Val Gln Ile
    50                  55                  60 caa ccg gta ttc aat gaa tta tac gcc cgt att acc caa gat atg gcc    240
Gln Pro Val Phe Asn Glu Leu Tyr Ala Arg Ile Thr Gln Asp Met Ala
65                  70                  75                  80 caa cct gat tct tat tta cat aaa aca act gaa gcg tta gct cta tca    288
Gln Pro Asp Ser Tyr Leu His Lys Thr Thr Glu Ala Leu Ala Leu Ser
                85                  90                  95 gat tcc gag ttt act gga aaa ctg tgg tct cta tac ctt gct acc tta    336
Asp Ser Glu Phe Thr Gly Lys Leu Trp Ser Leu Tyr Leu Ala Thr Leu
            100                 105                 110 aaa tct gca cag tac aaa aag cag aat ttt agg cta ggt ata ttt aga    384
Lys Ser Ala Gln Tyr Lys Lys Gln Asn Phe Arg Leu Gly Ile Phe Arg
        115                 120                 125 tca gat tat ttg att gat aag aaa aag ggt act gaa cag att aag caa    432
Ser Asp Tyr Leu Ile Asp Lys Lys Lys Gly Thr Glu Gln Ile Lys Gln
    130                 135                 140 gtc gag ttt aat aca gtg tca gtg tca ttt gca ggc ctt agc gag aaa    480
Val Glu Phe Asn Thr Val Ser Val Ser Phe Ala Gly Leu Ser Glu Lys
145                 150                 155                 160 gtt gat aga ttg cac tct tat tta aat agg gca aac aag tac gat cct    528
Val Asp Arg Leu His Ser Tyr Leu Asn Arg Ala Asn Lys Tyr Asp Pro
                165                 170                 175 aaa gga cca att tat aat gat caa aat atg gtc att tct gat tca gga    576
Lys Gly Pro Ile Tyr Asn Asp Gln Asn Met Val Ile Ser Asp Ser Gly
            180                 185                 190
```

```
                                                    -continued tac ctt ttg tct aag gca ttg gcc aaa gct gtg gaa tcg tat aag tca         624
Tyr Leu Leu Ser Lys Ala Leu Ala Lys Ala Val Glu Ser Tyr Lys Ser
            195                 200                 205 caa caa agt tct tct aca act agt gat cct att gtc gca ttc att gtg         672
Gln Gln Ser Ser Ser Thr Thr Ser Asp Pro Ile Val Ala Phe Ile Val
        210                 215                 220 caa aga aac gag aga aat gtg ttt gat caa aag gtc ttg gaa ttg aat         720
Gln Arg Asn Glu Arg Asn Val Phe Asp Gln Lys Val Leu Glu Leu Asn
225                 230                 235                 240 ctg ttg gaa aaa ttc ggt acc aaa tct gtt agg ttg acg ttt gat gat         768
Leu Leu Glu Lys Phe Gly Thr Lys Ser Val Arg Leu Thr Phe Asp Asp
                245                 250                 255 gtt aac gat aaa ttg ttc att gat gat aaa acg gga aag ctt ttc att         816
Val Asn Asp Lys Leu Phe Ile Asp Asp Lys Thr Gly Lys Leu Phe Ile
            260                 265                 270 agg gac aca gag cag gaa ata gcg gtg gtt tat tac aga acg ggt tac         864
Arg Asp Thr Glu Gln Glu Ile Ala Val Val Tyr Tyr Arg Thr Gly Tyr
        275                 280                 285 aca acc act gat tac acg tcc gaa aag gac tgg gag gca aga cta ttc         912
Thr Thr Thr Asp Tyr Thr Ser Glu Lys Asp Trp Glu Ala Arg Leu Phe
    290                 295                 300 ctc gaa aaa agt ttc gca ata aag gcc cca gat tta ctc act caa tta         960
Leu Glu Lys Ser Phe Ala Ile Lys Ala Pro Asp Leu Leu Thr Gln Leu
305                 310                 315                 320 tct ggc tcc aag aaa att cag caa ttg ttg aca gat gag ggc gta tta        1008
Ser Gly Ser Lys Lys Ile Gln Gln Leu Leu Thr Asp Glu Gly Val Leu
                325                 330                 335 ggt aaa tac atc tcc gat gct gag aaa aag agt agt ttg tta aaa act        1056
Gly Lys Tyr Ile Ser Asp Ala Glu Lys Lys Ser Ser Leu Leu Lys Thr
            340                 345                 350 ttt gtc aaa ata tat ccc ttg gat gat acg aag ctt ggc agg gaa ggc        1104
Phe Val Lys Ile Tyr Pro Leu Asp Asp Thr Lys Leu Gly Arg Glu Gly
        355                 360                 365 aag agg ctg gca tta agt gag ccc tct aaa tac gtg tta aaa cca cag        1152
Lys Arg Leu Ala Leu Ser Glu Pro Ser Lys Tyr Val Leu Lys Pro Gln
    370                 375                 380 cgg gaa ggt ggc gga aac aat gtt tat aaa gaa aat att cct aat ttt        1200
Arg Glu Gly Gly Gly Asn Asn Val Tyr Lys Glu Asn Ile Pro Asn Phe
385                 390                 395                 400 ttg aaa ggt atc gaa gaa cgt cac tgg gat gca tat att ctc atg gag        1248
Leu Lys Gly Ile Glu Glu Arg His Trp Asp Ala Tyr Ile Leu Met Glu
                405                 410                 415 ttg att gaa cca gag ttg aat gaa aat aat att ata tta cgt gat aac        1296
Leu Ile Glu Pro Glu Leu Asn Glu Asn Asn Ile Ile Leu Arg Asp Asn
            420                 425                 430 aaa tct tac aac gaa cca atc atc agt gaa cta gga att tat ggt tgc        1344
Lys Ser Tyr Asn Glu Pro Ile Ile Ser Glu Leu Gly Ile Tyr Gly Cys
        435                 440                 445 gtt cta ttt aac gac gag caa gtt tta tcg aac gaa ttt agt ggc tca        1392
Val Leu Phe Asn Asp Glu Gln Val Leu Ser Asn Glu Phe Ser Gly Ser
    450                 455                 460 tta cta aga tcc aaa ttt aat act tca aat gaa ggt gga gtg gcg gca        1440
Leu Leu Arg Ser Lys Phe Asn Thr Ser Asn Glu Gly Gly Val Ala Ala
465                 470                 475                 480 gga ttc gga tgt ttg gac agt att att ctt tac tag gtgtacatgt            1486
Gly Phe Gly Cys Leu Asp Ser Ile Ile Leu Tyr
                485                 490 actatacaca tagatgctag gaagatgatg ctagaacttg attaacaatt agttaaggaa      1546
tatataatca cacttctaca taaatttgct gttttaggct cattccttct ttctttcacc      1606
```

```
ctttagtagc gaagtacacc atttagctgc accaacagtg ttgctagata tggtgactat    1666
tgtgaagaag ggtattaact ctagtagacc ggcagacata ccgaaacata tgaaacttgc    1726
gtaatgctcg tactgaaaat ctttggcctg tttcttactg aatccctta gtaaaaagta    1786 cctctgcaaa taggtaaagg ttcttttgg ggccattagt tgatttgcca agattggtcc    1846
tacaatagga attagcgaca gtaatgttag tgaagtaaaa ttggagactt taaaaaacat    1906
tctgaatagt aatctgggaa tcttaaaaat ccgacttccc tttattgtgt tgaaatttct    1966
caccgcatca ggttcatcga tttttctatg tggcttttgt ggtttaggca ataccttcac    2026
ctcgtttaga aattcatctt ggtcttgcaa caccaaagat atatcaaata tctgattcgt    2086
aatatgggtc aggaccagtg ttctacaaac aaaggcagtc aagacattcg tttgtaaaat    2146
ccattgaata tgaaccagta tcacaccaag aggccctaat aacagtatgg cccatgtcac    2206
taaaagcggt acaagtgtga cataaaagag accagcaata gtgacaaaaa tcagggcata    2266 gcaaccgca aacagtaaaa tatgcttcca ataaacagga ttcgtcagca cttcataaaa    2326
cccctacggt taacaaataa aaattaaata tgttagtcat aaaacaagtc atatcaatgc    2386
aaacaaaaat catgtactta ctaagaatgg gtagataaat gctcttgagt tgaaaatttc    2446
tttaatgaag tttttctaa                                                 2466
```

<210> SEQ ID NO 2
<211> LENGTH: 491
<212> TYPE: PRT
<213> ORGANISM: Saccharomyces cerevisiae

<400> SEQUENCE: 2

```
Met Ala His Tyr Pro Pro Ser Lys Asp Gln Leu Asn Glu Leu Ile Gln
1               5                   10                  15

Glu Val Asn Gln Trp Ala Ile Thr Asn Gly Leu Ser Met Tyr Pro Pro
                20                  25                  30

Lys Phe Glu Glu Asn Pro Ser Asn Ala Ser Val Ser Pro Val Thr Ile
            35                  40                  45

Tyr Pro Thr Pro Ile Pro Arg Lys Cys Phe Asp Glu Ala Val Gln Ile
        50                  55                  60

Gln Pro Val Phe Asn Glu Leu Tyr Ala Arg Ile Thr Gln Asp Met Ala
65                  70                  75                  80

Gln Pro Asp Ser Tyr Leu His Lys Thr Thr Glu Ala Leu Ala Leu Ser
                85                  90                  95

Asp Ser Glu Phe Thr Gly Lys Leu Trp Ser Leu Tyr Leu Ala Thr Leu
            100                 105                 110

Lys Ser Ala Gln Tyr Lys Lys Gln Asn Phe Arg Leu Gly Ile Phe Arg
        115                 120                 125

Ser Asp Tyr Leu Ile Asp Lys Lys Gly Thr Glu Gln Ile Lys Gln
    130                 135                 140

Val Glu Phe Asn Thr Val Ser Val Ser Phe Ala Gly Leu Ser Glu Lys
145                 150                 155                 160

Val Asp Arg Leu His Ser Tyr Leu Asn Arg Ala Asn Lys Tyr Asp Pro
                165                 170                 175

Lys Gly Pro Ile Tyr Asn Asp Gln Asn Met Val Ile Ser Asp Ser Gly
            180                 185                 190

Tyr Leu Leu Ser Lys Ala Leu Ala Lys Ala Val Glu Ser Tyr Lys Ser
        195                 200                 205

Gln Gln Ser Ser Ser Thr Thr Ser Asp Pro Ile Val Ala Phe Ile Val
    210                 215                 220
```

-continued

Gln Arg Asn Glu Arg Asn Val Phe Asp Gln Lys Val Leu Glu Leu Asn
225                 230                 235                 240

Leu Leu Glu Lys Phe Gly Thr Lys Ser Val Arg Leu Thr Phe Asp Asp
            245                 250                 255

Val Asn Asp Lys Leu Phe Ile Asp Asp Lys Thr Gly Lys Leu Phe Ile
                260                 265                 270

Arg Asp Thr Glu Gln Glu Ile Ala Val Val Tyr Tyr Arg Thr Gly Tyr
            275                 280                 285

Thr Thr Thr Asp Tyr Thr Ser Glu Lys Asp Trp Glu Ala Arg Leu Phe
        290                 295                 300

Leu Glu Lys Ser Phe Ala Ile Lys Ala Pro Asp Leu Leu Thr Gln Leu
305                 310                 315                 320

Ser Gly Ser Lys Lys Ile Gln Gln Leu Leu Thr Asp Glu Gly Val Leu
                325                 330                 335

Gly Lys Tyr Ile Ser Asp Ala Glu Lys Lys Ser Ser Leu Leu Lys Thr
            340                 345                 350

Phe Val Lys Ile Tyr Pro Leu Asp Asp Thr Lys Leu Gly Arg Glu Gly
        355                 360                 365

Lys Arg Leu Ala Leu Ser Glu Pro Ser Lys Tyr Val Leu Lys Pro Gln
        370                 375                 380

Arg Glu Gly Gly Gly Asn Asn Val Tyr Lys Glu Asn Ile Pro Asn Phe
385                 390                 395                 400

Leu Lys Gly Ile Glu Glu Arg His Trp Asp Ala Tyr Ile Leu Met Glu
                405                 410                 415

Leu Ile Glu Pro Glu Leu Asn Glu Asn Asn Ile Ile Leu Arg Asp Asn
            420                 425                 430

Lys Ser Tyr Asn Glu Pro Ile Ile Ser Glu Leu Gly Ile Tyr Gly Cys
        435                 440                 445

Val Leu Phe Asn Asp Glu Gln Val Leu Ser Asn Glu Phe Ser Gly Ser
        450                 455                 460

Leu Leu Arg Ser Lys Phe Asn Thr Ser Asn Glu Gly Gly Val Ala Ala
465                 470                 475                 480

Gly Phe Gly Cys Leu Asp Ser Ile Ile Leu Tyr
                485                 490

<210> SEQ ID NO 3
<211> LENGTH: 1923
<212> TYPE: DNA
<213> ORGANISM: Saccharomyces cerevisiae
<220> FEATURE:
<221> NAME/KEY: CDS
<222> LOCATION: (1)..(1920)

<400> SEQUENCE: 3

| atg agg aga gag agg caa agg atg atg agt ttc gag gac aag gac aag | 48 |
|---|---|
| Met Arg Arg Glu Arg Gln Arg Met Met Ser Phe Glu Asp Lys Asp Lys | |
| 1               5                   10                  15 | |

| gac gac ctt gac aat agt aat agt aat aac agc agt gaa atg aca gat | 96 |
|---|---|
| Asp Asp Leu Asp Asn Ser Asn Ser Asn Asn Ser Ser Glu Met Thr Asp | |
|             20                  25                  30 | |

| acg gcg atg atg cca cca tta aag aga ttg ctt att acg ggc agt agc | 144 |
|---|---|
| Thr Ala Met Met Pro Pro Leu Lys Arg Leu Leu Ile Thr Gly Ser Ser | |
|         35                  40                  45 | |

| gat gat ttg gca caa gga tca tcg ggt aag aag aag atg acg atg gcg | 192 |
|---|---|
| Asp Asp Leu Ala Gln Gly Ser Ser Gly Lys Lys Lys Met Thr Met Ala | |
|     50                  55                  60 | |

```
acg agg tcg cca tcg tca tca ccc gat ttg gcg aca aac gac agc ggc      240
Thr Arg Ser Pro Ser Ser Ser Pro Asp Leu Ala Thr Asn Asp Ser Gly
 65                  70                  75                  80 act agg gta cag cca ttg cca gaa tat aac ttc acc aag ttc tgc tat      288
Thr Arg Val Gln Pro Leu Pro Glu Tyr Asn Phe Thr Lys Phe Cys Tyr
                     85                  90                  95 cgg cat aac ccg gac att cag ttc tca cca act cat aca gcg tgc tac      336
Arg His Asn Pro Asp Ile Gln Phe Ser Pro Thr His Thr Ala Cys Tyr
                    100                 105                 110 aag cag gat ttg aaa cga acg caa gag att aat gct aat atc gcg aag      384
Lys Gln Asp Leu Lys Arg Thr Gln Glu Ile Asn Ala Asn Ile Ala Lys
                115                 120                 125 cta ccc ctg cag gag caa tcc gac atc cac cac att atc tcg aag tac      432
Leu Pro Leu Gln Glu Gln Ser Asp Ile His His Ile Ile Ser Lys Tyr
130                 135                 140 agc aat tcc aat gac aag ata cgg aag ctg att ctg gat ggg atc cta      480
Ser Asn Ser Asn Asp Lys Ile Arg Lys Leu Ile Leu Asp Gly Ile Leu
145                 150                 155                 160 tcg acg agt tgc ttc cca cag ctt tcc tac att tcg tca ctc gtt aca      528
Ser Thr Ser Cys Phe Pro Gln Leu Ser Tyr Ile Ser Ser Leu Val Thr
                    165                 170                 175 cac atg atc aag atc gac ttc atc agc att ctg ccg cag gag ctg tcg      576
His Met Ile Lys Ile Asp Phe Ile Ser Ile Leu Pro Gln Glu Leu Ser
                    180                 185                 190 ctg aag atc ttg agt tat ctg gat tgc caa tct ctt tgc aac gcc acg      624
Leu Lys Ile Leu Ser Tyr Leu Asp Cys Gln Ser Leu Cys Asn Ala Thr
                195                 200                 205 aga gtg tgc cgc aag tgg cag aag ctc gcg gat gac gac agg gta tgg      672
Arg Val Cys Arg Lys Trp Gln Lys Leu Ala Asp Asp Asp Arg Val Trp
                210                 215                 220 tac cac atg tgc gag cag cac ata gac agg aaa tgt ccc aac tgt ggc      720
Tyr His Met Cys Glu Gln His Ile Asp Arg Lys Cys Pro Asn Cys Gly
225                 230                 235                 240 tgg ggg ctg cct ctt ttg cac atg aaa cgt gcg cgg ata caa cag aat      768
Trp Gly Leu Pro Leu Leu His Met Lys Arg Ala Arg Ile Gln Gln Asn
                    245                 250                 255 agt aca gga tct agc agc aac gca gat atc cag acg caa act acg cga      816
Ser Thr Gly Ser Ser Ser Asn Ala Asp Ile Gln Thr Gln Thr Thr Arg
                260                 265                 270 cct tgg aaa gtc atc tac aga gaa cgg ttc aaa gtg gag tca aac tgg      864
Pro Trp Lys Val Ile Tyr Arg Glu Arg Phe Lys Val Glu Ser Asn Trp
                275                 280                 285 aga aag ggc cac tgc agg att cag gaa ttc aag ggc cac atg gat ggt      912
Arg Lys Gly His Cys Arg Ile Gln Glu Phe Lys Gly His Met Asp Gly
            290                 295                 300 gtg tta acg ctc cag ttt aac tac agg ctt ttg ttc aca ggc tcg tac      960
Val Leu Thr Leu Gln Phe Asn Tyr Arg Leu Leu Phe Thr Gly Ser Tyr
305                 310                 315                 320 gac tcc acc ata ggt ata tgg gac tta ttc acg ggg aag cta ata cga     1008
Asp Ser Thr Ile Gly Ile Trp Asp Leu Phe Thr Gly Lys Leu Ile Arg
                325                 330                 335 agg ctc agc ggc cat tcg gac ggc gtc aag aca tta tat ttt gac gat     1056
Arg Leu Ser Gly His Ser Asp Gly Val Lys Thr Leu Tyr Phe Asp Asp
                340                 345                 350 aga aag ctg att acg ggc tcg ctc gac aag acg atc cgt gtt tgg aac     1104
Arg Lys Leu Ile Thr Gly Ser Leu Asp Lys Thr Ile Arg Val Trp Asn
                355                 360                 365 tac ata acc ggt gaa tgc att tcc acg tat cga ggc cac tcg gat agc     1152
Tyr Ile Thr Gly Glu Cys Ile Ser Thr Tyr Arg Gly His Ser Asp Ser
                370                 375                 380
```

```
gtt ctg agc gta gat tca tac cag aag gtt atc gtt tcc ggc agt gct      1200
Val Leu Ser Val Asp Ser Tyr Gln Lys Val Ile Val Ser Gly Ser Ala
385                 390                 395                 400 gac aag acg gtc aag gta tgg cac gtg gag tcc agg aca tgc tac acc      1248
Asp Lys Thr Val Lys Val Trp His Val Glu Ser Arg Thr Cys Tyr Thr
                405                 410                 415 ttg aga ggc cac acg gaa tgg gtt aat tgc gtc aaa ttg cat ccg aaa      1296
Leu Arg Gly His Thr Glu Trp Val Asn Cys Val Lys Leu His Pro Lys
            420                 425                 430 agc ttt tca tgt ttt agt tgc agt gac gat acc aca atc cga atg tgg      1344
Ser Phe Ser Cys Phe Ser Cys Ser Asp Asp Thr Thr Ile Arg Met Trp
        435                 440                 445 gat atc agg acc aat tca tgc cta aaa gtg ttc agg ggt cat gta ggg      1392
Asp Ile Arg Thr Asn Ser Cys Leu Lys Val Phe Arg Gly His Val Gly
450                 455                 460 cag gtg caa aag atc ata ccg ctt acc att aag gat gta gag aat cta      1440
Gln Val Gln Lys Ile Ile Pro Leu Thr Ile Lys Asp Val Glu Asn Leu
465                 470                 475                 480 gcc acc gac aac act tct gat ggc agc tct ccg cag gat gac cca aca      1488
Ala Thr Asp Asn Thr Ser Asp Gly Ser Ser Pro Gln Asp Asp Pro Thr
                485                 490                 495 atg act gat ggt gca gac gaa tca gac aca ccg tcg aac gag caa gaa      1536
Met Thr Asp Gly Ala Asp Glu Ser Asp Thr Pro Ser Asn Glu Gln Glu
            500                 505                 510 act gtc tta gat gaa aac ata cct tat cca aca cat cta cta tct tgc      1584
Thr Val Leu Asp Glu Asn Ile Pro Tyr Pro Thr His Leu Leu Ser Cys
        515                 520                 525 gga ctg gat aac aca atc aaa cta tgg gac gtc aaa acc ggt aaa tgc      1632
Gly Leu Asp Asn Thr Ile Lys Leu Trp Asp Val Lys Thr Gly Lys Cys
530                 535                 540 ata aga aca cag ttt ggg cac gtg gaa ggt gtt tgg gac atc gcc gct      1680
Ile Arg Thr Gln Phe Gly His Val Glu Gly Val Trp Asp Ile Ala Ala
545                 550                 555                 560 gac aac ttc aga att ata agt ggt tct cac gac gga agc att aag gtc      1728
Asp Asn Phe Arg Ile Ile Ser Gly Ser His Asp Gly Ser Ile Lys Val
                565                 570                 575 tgg gac ttg caa agc ggg aag tgt atg cac acg ttc aac ggt cga aga      1776
Trp Asp Leu Gln Ser Gly Lys Cys Met His Thr Phe Asn Gly Arg Arg
            580                 585                 590 cta caa aga gaa act cag cac aca caa aca caa tcc ttg ggt gat aaa      1824
Leu Gln Arg Glu Thr Gln His Thr Gln Thr Gln Ser Leu Gly Asp Lys
        595                 600                 605 gtc gcc cct atc gct tgt gtt tgt att gga gat tca gaa tgc ttt agt      1872
Val Ala Pro Ile Ala Cys Val Cys Ile Gly Asp Ser Glu Cys Phe Ser
610                 615                 620 ggt gat gaa ttt ggg tgc gta aaa atg tac aaa ttc gat ctc aat gat      1920
Gly Asp Glu Phe Gly Cys Val Lys Met Tyr Lys Phe Asp Leu Asn Asp
625                 630                 635                 640 tag                                                                  1923

<210> SEQ ID NO 4
<211> LENGTH: 640
<212> TYPE: PRT
<213> ORGANISM: Saccharomyces cerevisiae

<400> SEQUENCE: 4

Met Arg Arg Glu Arg Gln Arg Met Met Ser Phe Glu Asp Lys Asp Lys
1               5                   10                  15

Asp Asp Leu Asp Asn Ser Asn Ser Asn Asn Ser Ser Glu Met Thr Asp
            20                  25                  30
```

```
Thr Ala Met Met Pro Pro Leu Lys Arg Leu Leu Ile Thr Gly Ser Ser
        35                  40                  45

Asp Asp Leu Ala Gln Gly Ser Ser Gly Lys Lys Met Thr Met Ala
    50                  55                  60

Thr Arg Ser Pro Ser Ser Pro Asp Leu Ala Thr Asn Asp Ser Gly
65                  70                  75                  80

Thr Arg Val Gln Pro Leu Pro Glu Tyr Asn Phe Thr Lys Phe Cys Tyr
                85                  90                  95

Arg His Asn Pro Asp Ile Gln Phe Ser Pro Thr His Thr Ala Cys Tyr
                100                 105                 110

Lys Gln Asp Leu Lys Arg Thr Gln Glu Ile Asn Ala Asn Ile Ala Lys
                115                 120                 125

Leu Pro Leu Gln Glu Gln Ser Asp Ile His His Ile Ile Ser Lys Tyr
    130                 135                 140

Ser Asn Ser Asn Asp Lys Ile Arg Lys Leu Ile Leu Asp Gly Ile Leu
145                 150                 155                 160

Ser Thr Ser Cys Phe Pro Gln Leu Ser Tyr Ile Ser Ser Leu Val Thr
                165                 170                 175

His Met Ile Lys Ile Asp Phe Ile Ser Ile Leu Pro Gln Glu Leu Ser
                180                 185                 190

Leu Lys Ile Leu Ser Tyr Leu Asp Cys Gln Ser Leu Cys Asn Ala Thr
    195                 200                 205

Arg Val Cys Arg Lys Trp Gln Lys Leu Ala Asp Asp Asp Arg Val Trp
    210                 215                 220

Tyr His Met Cys Glu Gln His Ile Asp Arg Lys Cys Pro Asn Cys Gly
225                 230                 235                 240

Trp Gly Leu Pro Leu Leu His Met Lys Arg Ala Arg Ile Gln Gln Asn
                245                 250                 255

Ser Thr Gly Ser Ser Ser Asn Ala Asp Ile Gln Thr Gln Thr Thr Arg
                260                 265                 270

Pro Trp Lys Val Ile Tyr Arg Glu Arg Phe Lys Val Glu Ser Asn Trp
        275                 280                 285

Arg Lys Gly His Cys Arg Ile Gln Glu Phe Lys Gly His Met Asp Gly
        290                 295                 300

Val Leu Thr Leu Gln Phe Asn Tyr Arg Leu Leu Phe Thr Gly Ser Tyr
305                 310                 315                 320

Asp Ser Thr Ile Gly Ile Trp Asp Leu Phe Thr Gly Lys Leu Ile Arg
                325                 330                 335

Arg Leu Ser Gly His Ser Asp Gly Val Lys Thr Leu Tyr Phe Asp Asp
        340                 345                 350

Arg Lys Leu Ile Thr Gly Ser Leu Asp Lys Thr Ile Arg Val Trp Asn
        355                 360                 365

Tyr Ile Thr Gly Glu Cys Ile Ser Thr Tyr Arg Gly His Ser Asp Ser
        370                 375                 380

Val Leu Ser Val Asp Ser Tyr Gln Lys Val Ile Val Ser Gly Ser Ala
385                 390                 395                 400

Asp Lys Thr Val Lys Val Trp His Val Glu Ser Arg Thr Cys Tyr Thr
                405                 410                 415

Leu Arg Gly His Thr Glu Trp Val Asn Cys Val Lys Leu His Pro Lys
                420                 425                 430

Ser Phe Ser Cys Phe Ser Cys Ser Asp Asp Thr Thr Ile Arg Met Trp
    435                 440                 445
```

-continued

```
Asp Ile Arg Thr Asn Ser Cys Leu Lys Val Phe Arg Gly His Val Gly
    450                 455                 460
Gln Val Gln Lys Ile Ile Pro Leu Thr Ile Lys Asp Val Glu Asn Leu
465                 470                 475                 480
Ala Thr Asp Asn Thr Ser Asp Gly Ser Ser Pro Gln Asp Asp Pro Thr
                485                 490                 495
Met Thr Asp Gly Ala Asp Glu Ser Asp Thr Pro Ser Asn Glu Gln Glu
            500                 505                 510
Thr Val Leu Asp Glu Asn Ile Pro Tyr Pro Thr His Leu Leu Ser Cys
        515                 520                 525
Gly Leu Asp Asn Thr Ile Lys Leu Trp Asp Val Lys Thr Gly Lys Cys
    530                 535                 540
Ile Arg Thr Gln Phe Gly His Val Glu Gly Val Trp Asp Ile Ala Ala
545                 550                 555                 560
Asp Asn Phe Arg Ile Ile Ser Gly Ser His Asp Gly Ser Ile Lys Val
                565                 570                 575
Trp Asp Leu Gln Ser Gly Lys Cys Met His Thr Phe Asn Gly Arg Arg
            580                 585                 590
Leu Gln Arg Glu Thr Gln His Thr Gln Thr Gln Ser Leu Gly Asp Lys
        595                 600                 605
Val Ala Pro Ile Ala Cys Val Cys Ile Gly Asp Ser Glu Cys Phe Ser
    610                 615                 620
Gly Asp Glu Phe Gly Cys Val Lys Met Tyr Lys Phe Asp Leu Asn Asp
625                 630                 635                 640
```

```
<210> SEQ ID NO 5
<211> LENGTH: 29
<212> TYPE: DNA
<213> ORGANISM: Artificial Sequence
<220> FEATURE:
<223> OTHER INFORMATION: Synthetic DNA

<400> SEQUENCE: 5
aatgcaaacc gctgctcaat cttcttcaa                                         29

<210> SEQ ID NO 6
<211> LENGTH: 29
<212> TYPE: DNA
<213> ORGANISM: Artificial Sequence
<220> FEATURE:
<223> OTHER INFORMATION: Synthetic DNA

<400> SEQUENCE: 6
tgacccattc aaactttctg gtgctcaag                                         29

<210> SEQ ID NO 7
<211> LENGTH: 20
<212> TYPE: DNA
<213> ORGANISM: Artificial Sequence
<220> FEATURE:
<223> OTHER INFORMATION: Synthetic DNA

<400> SEQUENCE: 7
gtcgccttgg acttcgaaca                                                   20

<210> SEQ ID NO 8
<211> LENGTH: 24
<212> TYPE: DNA
<213> ORGANISM: Artificial Sequence
<220> FEATURE:
<223> OTHER INFORMATION: Synthetic DNA
```

-continued

```
<400> SEQUENCE: 8
tctggaagtt cgtaggattt ttca                                              24

<210> SEQ ID NO 9
<211> LENGTH: 20
<212> TYPE: DNA
<213> ORGANISM: Artificial Sequence
<220> FEATURE:
<223> OTHER INFORMATION: Synthetic DNA

<400> SEQUENCE: 9
accaaatgcc gacaaggaaa                                                   20

<210> SEQ ID NO 10
<211> LENGTH: 26
<212> TYPE: DNA
<213> ORGANISM: Artificial Sequence
<220> FEATURE:
<223> OTHER INFORMATION: Synthetic DNA

<400> SEQUENCE: 10
gttagaggca agctttaaat tgtcaa                                            26

<210> SEQ ID NO 11
<211> LENGTH: 40
<212> TYPE: DNA
<213> ORGANISM: Artificial Sequence
<220> FEATURE:
<223> OTHER INFORMATION: Synthetic DNA

<400> SEQUENCE: 11
atggcacact atccaccttc aaagtgccca tcagtgttca                             40

<210> SEQ ID NO 12
<211> LENGTH: 40
<212> TYPE: DNA
<213> ORGANISM: Artificial Sequence
<220> FEATURE:
<223> OTHER INFORMATION: Synthetic DNA

<400> SEQUENCE: 12
ctagtaaaga ataatactgt ttaaagttga tttagataag                             40
```